United States Patent [19]

Yang et al.

[11] Patent Number: 5,267,152

[45] Date of Patent: Nov. 30, 1993

[54] NON-INVASIVE METHOD AND APPARATUS FOR MEASURING BLOOD GLUCOSE CONCENTRATION

[76] Inventors: Won S. Yang, 6-405, Donga APT., 26, Chang-dong, Dobong-ku, Seoul; Yoon O. Kim, 865-2, Daerim-dong, Youngdungpo-ku, Seoul, both of Rep. of Korea

[21] Appl. No.: 604,800

[22] Filed: Oct. 26, 1990

[30] Foreign Application Priority Data

Oct. 28, 1989 [KR] Rep. of Korea ............... 89-15584
Jul. 24, 1990 [KR] Rep. of Korea ............... 90-11241

[51] Int. Cl.$^5$ ............................................ G06F 15/42
[52] U.S. Cl. ..................... 364/413.09; 364/413.07; 128/633; 128/664; 250/339; 250/341; 356/39
[58] Field of Search ............ 128/632, 633, 637, 664; 364/413.01, 413.03, 413.07, 413.08, 413.09; 250/341, 339; 356/40, 41, 39

[56] References Cited

U.S. PATENT DOCUMENTS

| | | | |
|---|---|---|---|
| 4,169,676 | 10/1979 | Kaiser ................. | 128/633 |
| 4,655,225 | 4/1987 | Dähner et al. ......... | 128/633 |
| 4,714,080 | 12/1987 | Edgar, Jr. et al. .... | 128/633 |
| 4,759,369 | 7/1988 | Taylor ................ | 128/664 |
| 4,800,885 | 1/1989 | Johnson .............. | 364/413.09 |
| 4,882,492 | 11/1989 | Schlager ............. | 128/637 |
| 4,913,150 | 4/1990 | Cheung et al. ........ | 128/664 |
| 4,975,581 | 12/1990 | Robinson et al. ...... | 250/339 |
| 5,028,787 | 7/1991 | Rosenthal et al. ..... | 250/341 |
| 5,054,487 | 10/1991 | Clarke ............... | 128/633 |
| 5,070,874 | 12/1991 | Barnes et al. ........ | 128/633 |
| 5,077,476 | 12/1991 | Rosenthal ............ | 250/341 |
| 5,187,368 | 2/1993 | Galante et al. ....... | 250/339 |

Primary Examiner—Roy N. Envall, Jr.
Assistant Examiner—Jennifer L. Hazard
Attorney, Agent, or Firm—Hecker & Harriman

[57] ABSTRACT

A method and apparatus for measuring blood glucose concentration by irradiating blood vessels with electromagnetic radiation, where the method and apparatus uses near-infrared radiation diffuse-reflection laser spectroscopy. This invention uses electromagnetic radiation of a wavelength that is transmitted through the skin to the measurement region, for example, a blood vessel. Since skin is mostly composed of water ($H_2O$), which absorbs infrared radiation in nearly the entire infrared spectral range, only radiation from a certain, narrow portion of the infrared spectral range called the "water transmission window" is transmitted through the skin. The present invention uses electromagnetic radiation with a wavelength of 1.3 $\mu$m-1.8 $\mu$m radiation from a semiconductor diode laser. When electromagnetic radiation of these wavelengths irradiates the skin, light is transmitted through the skin to the blood vessel where the light interacts with the heterogeneous components of the blood. The light transmitted to the blood is then diffusely reflected by the blood. The reflected light will have been modulated by the characteristic vibrations of the molecules which are major components of blood. The reflected light is detected and provided as a digital signal to a one-chip microcomputer. The one-chip microcomputer calculates a blood glucose concentration from the digital signal by reference to a calibration curve stored in the memory of the one-chip microcomputer. The one-chip microcomputer causes the calculated blood glucose concentration to be displayed on a digital display.

25 Claims, 2 Drawing Sheets

NON-INVASIVE METHOD AND APPARATUS FOR MEASURING BLOOD GLUCOSE CONCENTRATION

BACKGROUND OF THE INVENTION

I. Field of the Invention

The present invention relates to a method and apparatus for measuring blood glucose concentration, and more particularly, to a non-invasive technique for measuring blood glucose concentration using near-infrared radiation diffuse-reflection laser spectroscopy.

II Prior Art

Generally, diabetics measure blood glucose concentration two to eight times daily using a portable measurement apparatus consisting of a syringe (to obtain a blood sample) and appropriate reagents (to measure the amount of glucose in the blood). This is known as the "enzymatic" method or test.

The enzymatic test for glucose concentration is undesirable both because it requires that blood be drawn and because it is expensive. Less expensive techniques based on test paper have been introduced, but they are less accurate and still require that blood be drawn. Accordingly, research has been conducted to address these problems.

It is desired to provide a method for measuring blood glucose concentration that is accurate and does not require the drawing of blood.

Therefore, an object of the present invention is to provide a noninvasive technique for measuring blood glucose concentration, that is, to eliminate the need for drawing blood for this measurement.

A further object of the present invention is to provide a convenient, inexpensive, portable, easy-to-use apparatus for measuring blood glucose concentration.

SUMMARY OF THE INVENTION

The present invention is based on near-infrared radiation diffuse-reflection laser spectroscopy which measures blood glucose concentration by irradiating blood vessels with harmless electromagnetic radiation. This invention uses electromagnetic radiation of a wavelength that is transmitted through the skin to the measurement region, for example, a blood vessel. Since skin is mostly composed of water ($H_2O$), which absorbs infrared radiation in nearly the entire infrared spectral range, only radiation from a certain, narrow portion of the infrared spectral range called the "water transmission window" is transmitted through the skin.

Until recently, the water transmission window was thought to only include wavelengths between $3 \sim 5$ $\mu$m. However, according to investigations by the present inventors, the radiation which is able to reach a blood vessel through the water transmission window includes wavelengths between $1.3 \sim 1.9$ $\mu$m.

Accordingly, the present invention uses electromagnetic radiation with a wavelength of 1.3 $\mu$m-1.9 $\mu$m from a semiconductor diode laser. When electromagnetic radiation of these wavelengths irradiates the skin, light is transmitted through the skin to the blood vessel where the light interacts with the heterogeneous components of the blood. The light which reaches the blood is diffusely reflected by the blood. The reflected light will have been modulated by the characteristic vibrations of the molecules which are major components of blood.

In the present invention, the diffusely reflected light described above is collected by an integrating sphere. The photons (hv) collected as described above, are converted into an electrical signal by a detector, and that signal is supplied to a processing means, such as a one-chip microcomputer. The one-chip microcomputer calculates the blood glucose concentration using an accurate calibration method. Near infrared radiation is defined in the present invention (in accord with the International Union of Pure and Applied Chemistry (IUPAC) definition) as follows: frequency of about $10^{13} \sim 3.75 \times 10^{14}$ Hz; energy of about $0.951 \sim 35.8$ (Kcal/mol), $0.0412 \sim 1.55$ eV; wavelength of about $0.8 \sim 30$ $\mu$m. The present invention is based on physical and chemical principles describing the vibrational motion of the blood glucose molecules as measured with near-infrared radiation diffuse-reflection laser spectroscopy. Such vibrational motion includes both rotational and translational motion, and includes overtone vibrations and combination vibrations. Of these vibrations, the overtone vibrations are dominant.

The analysis method incorporated in the present invention includes a mathematical model based on multiple linear regression analysis and multivariate analysis as modified by the present inventors to determine the blood glucose concentration.

The mathematical algorithm used in the present invention is based on modifications of the above methods. The modifications are described by the following analytic function:

$$C_i = f(p, T, I, T_m, z, \ldots), \quad (1)$$

where $C_i$ is the blood glucose concentration, p is the laser diode output power, T is the transmission, I is the diode forward current, $T_m$ is the temperature of the laser diode, and z is the possible "intensity" due to other components of human tissue of non-invasive analysis of blood glucose. The operation parameters p, I and $T_m$ are used to calculate the blood glucose concentration.

Transformation of the parameters $X = p$, $Y = I, T_m$, and T, and $Z =$ "intensity" of other components in Equation (1), yields the following expression:

$$C_i = \alpha + \beta + X_a/X_g{}^*(1 + \Sigma\tau_{ij}{}^*(Y_a/Y_g)j) + \Sigma\delta_{ij}{}^* \cdot (Z_a/Z_g)j. \quad (2)$$

This is one form of the modified mathematical algorithm.

Each measurement supplies a data set consisting of certain values for X, Y, and Z. All original data Y and Z will be transformed and normalized to X as shown below:

$$Y_i' = X_{max} - (Y_{max} - Y_i)^*(X_{max} - X_{min})/(Y_{max} - Y_{min}). \quad (3)$$

where $\Delta X = \Delta Y$. In order to calibrate the measurement data(which lasts less than 40 seconds and comprises around 160 subdata), data will transferred and normalized to:

$$1/n * \sum_{i=1}^{n} Q_i$$

wherein $Q_i = (\pi_{i=j}{}^n R_j)^{1/m}$ and $R_j$ is $X_j$, $Y'_j$ and $Y'_j$ ($\pi$ is the geometrical sum).

For calibration, the data of several measurements taken from one or more persons are transformed and normalized again, in a very similar way as discussed above, using factors obtained using the arithmetic and geometric means. The first results show that the estimated error of the analysis, for an analytical range of glucose concentration between 40–400 mg/dl, is smaller than 0.05 relatively and on the other hand, the precision for the duplicated measurement is smaller than 0.04 relatively.

The present invention provides a method and apparatus for measuring blood glucose concentration, which has the advantage of ease of use and minimal expense for patients. The present invention has no consumable parts and is portable, allowing easy out-of-home testing. The present invention is more convenient than the prior art techniques. Also, this invention does not present the possible physical damage associated with the long-term use of syringes.

The measurement apparatus of the present invention can measure blood glucose concentration in a short time and unobtrusively. Therefore, the prior art techniques, with their inconvenience and expense are rendered obsolete.

This object and other objects of the present invention are achieved by measuring blood glucose concentration with a non-invasive technique, where:

a power source, for example a battery, is supplied to a one-chip microcomputer, a digital display, a laser diode power supply, a detector (as needed), and an optical unit (as needed) by means of a power switch. The one-chip microcomputer controls the laser diode power supply so that it gradually applies current at a stable voltage and temperature to a laser diode, which emits the necessary wavelengths of radiation. The laser is responsive to the start/reset switch. The one-chip microcomputer is operated so that the digital to analog (D/A) converter 10 controlled by said one-chip microcomputer and driving said laser diode power supply converts a digital control signal into an analog control signal.

Thus, the laser diode power supply causes a laser diode to emit a wavelength suitable for this measurement. The light from said laser diode is collimated, or otherwise optically controlled, separated and combined. The optically controlled light is used to irradiate the skin adjacent to a blood vessel. The light absorbed, dispersed and diffusely reflected by the blood back through the skin is collected by an integrating sphere. The photons collected by the integrating sphere are converted into an analog electrical signal by a detector. The analog electrical signal is transmitted to a preamplifier where the analog electrical signal is amplified. The amplified analog electrical signal is provided to an analog to digital (A/D) converter that converts the amplified analog electrical signal to a corresponding digital signal and outputs the digital signal to a one-chip microcomputer. The one-chip microcomputer calculates a blood glucose concentration from the digital signal by reference to a calibration curve stored in the memory of the one-chip microcomputer. The one-chip microcomputer causes the calculated blood glucose concentration to be displayed on a digital display.

An apparatus for measuring blood glucose concentration using a non-invasive technique according to the present invention comprises: one-chip microcomputer which controls the laser diode power supply so that current is gradually applied to a laser diode at a stable voltage while keeping the laser temperature constant. The microcomputer calculates the blood glucose concentration by comparing a detected value with a calibration curve stored in the microcomputer's memory. A D/A converter converts the digital control signal output from said microcomputer into an analog control signal for control of the laser diode power supply. The laser diode is the light source for the blood glucose measurement. There may be a plurality of laser diodes for emitting light of different wavelengths or for emitting light of like wavelengths in accordance with the current supplied from the laser diode power supply. A temperature controller, such as a peltier element, is connected between the laser diode power supply and the laser diode to control the temperature of the laser diode. An optical unit collimates the light emitted from the laser diode, or optically controls, separates and combines the light from the laser diode. An integrating sphere collects the light dispersed and diffusely reflected from the blood when the blood is illuminated through the skin by light from the optical unit. A detector converts the photons collected by the integrating sphere into an analog electrical value which is then amplified in the preamplifier. An A/D converter converts the electrical analog measurement value into a digital value. A digital display displays the blood glucose concentration calculated by the one-chip microcomputer.

BRIEF DESCRIPTION OF THE DRAWINGS

These and other objects and features of the present invention will be understood through the various embodiments by reference to the accompanying drawings in which.

DETAILED DESCRIPTION OF THE INVENTION

A preferred embodiment of a measurement apparatus according to the present invention will be described hereinafter with reference to the accompanying drawings.

Figure 1:
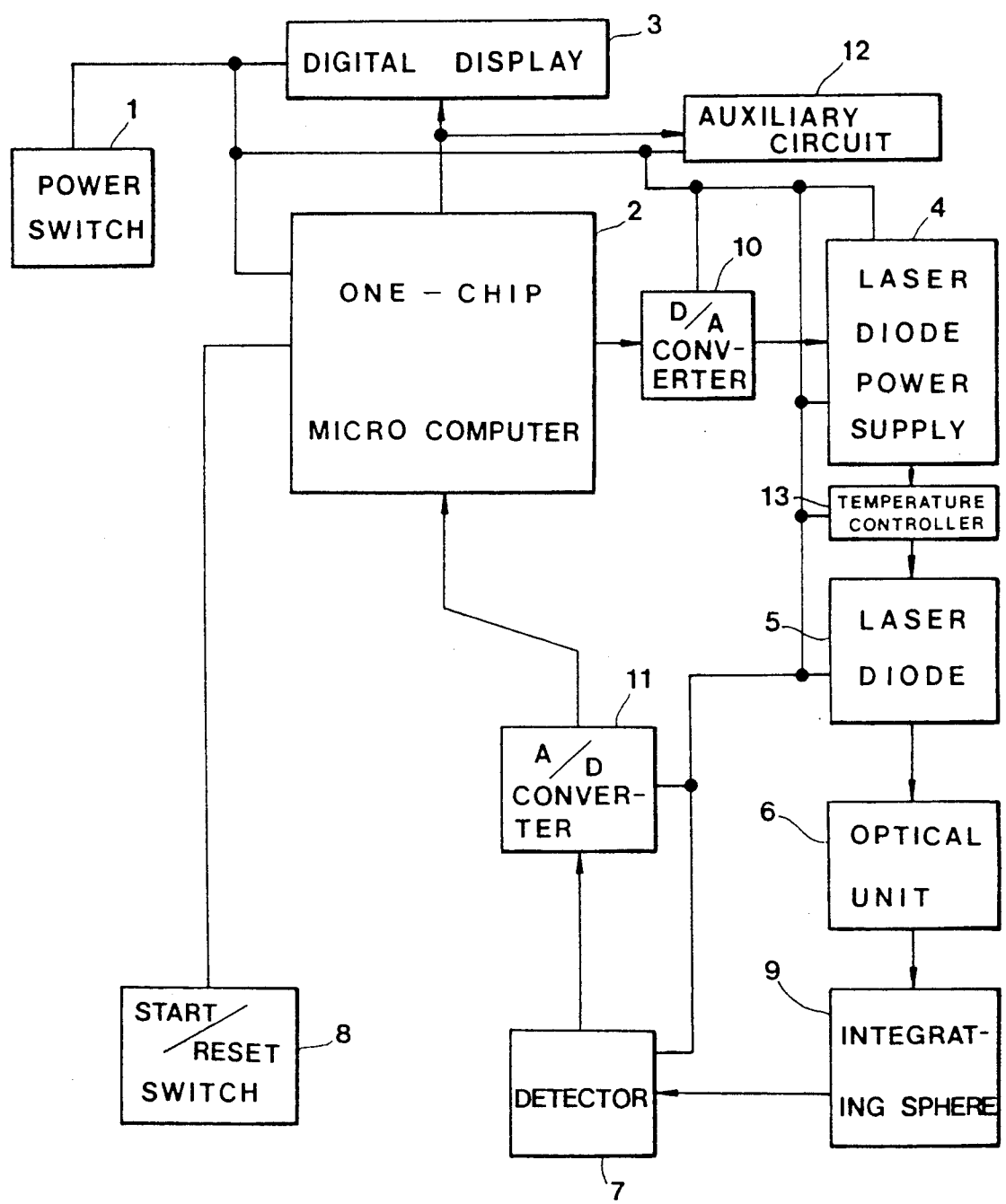
FIG. 1 is a block diagram showing an apparatus for measuring blood glucose concentration according to the present invention.
Figure 2:
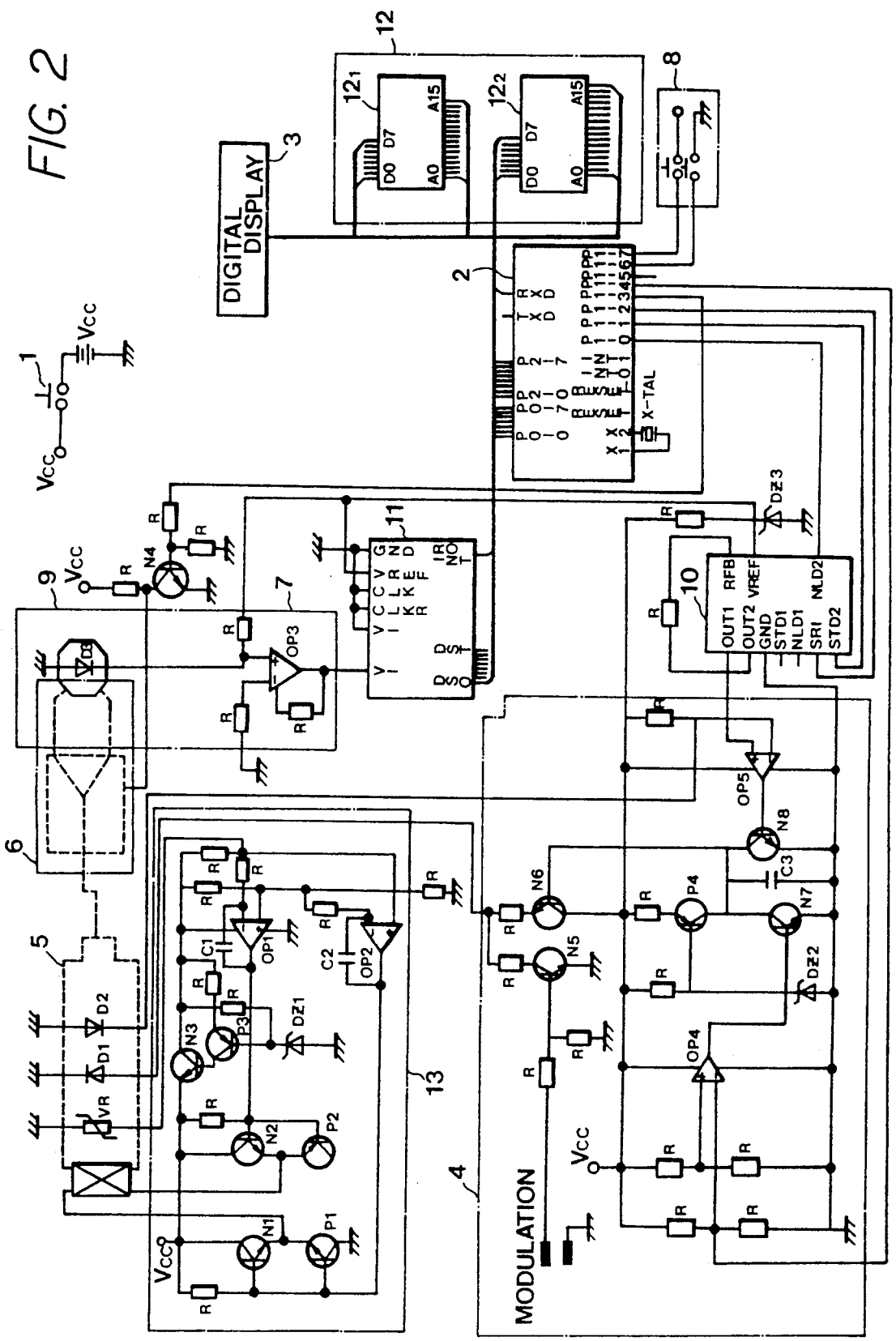
FIG. 2 is a detailed circuit diagram showing the apparatus for FIG. 1.

Referring to FIG. 1, when a power switch 1 is switched ON, power is supplied from the battery (not shown), (generally 4.5~9 V and is suited to a charging battery of 6 V among other possibilities) to a one-chip microcomputer 2. At the same time, the power source is supplied to a digital display 3, a laser diode power supply 4, and optical unit 6 (as needed).

If the start/reset switch 8 is then switched ON, the laser diode power supply 4 supplies the laser diode assembly 5 with power in accordance with the control signal supplied by the one-chip microcomputer 2. As a result, the laser diode current gradually increases until the current exceeds the threshold current (approximately 20 mA). Thus, the laser diode within laser diode assembly 5 starts emitting light.

The laser diode emits light, (for example, light having a wavelength of 1.3 $\mu$m–1.9 $\mu$m, of a wavelength necessary for a blood glucose concentration measurement. This wavelength is achieved by gradually increasing the current supplied within the range of approximately 20~200 mA at a stable voltage while maintaining a constant temperature in accordance with the operating characteristics of the laser diode. A peltier element 13 is used to control the temperature of the laser diode 5. The peltier element is connected between the laser diode power supply 4 and the laser diode 5. In the present invention, the laser diode assembly 5 is composed of between 1 and 30 individual laser diodes, and each may emit light of a different wavelength, or each may emit light of the same wavelength.

The collective diodes in the laser diode assembly 5 may be operated simultaneously or sequentially. In case of simultaneous operation, individual wavelengths of radiation will be selected, for example, using the Fourier Transform.

The light output from the collective diodes of the laser diode assembly 5 is supplied to an optical unit 6, and collimated, or the light is optically controlled, separated and combined. Thereafter, the light is passed through an integrating sphere 9 and divided in one or more directions.

The light which passes through the integrating sphere 9 irradiates the skin of a subject, or irradiates a reference head which was ready beforehand as the case may be. Here, the reference head is not necessarily needed. The head assembly (or simply the head) comprises the integration unit 9, the laser diode 5, the temperature controller 13, the optical unit 6 (if necessary), and the detector 7.

The light absorbed, dispersed, diffused and reflected by the blood is detected by a detector 7 after being collected by the integrating sphere 9. The integrating sphere is globular or of a like shape. Here, the size of integrating sphere 9, which collects the light dispersed and reflected from the blood, has a width, length and height under 2.56 cm, and is suitable for under 1.28 cm, and more particularly, may be smaller than 0.64 cm.

An electrical analog signal detected as above described is amplified by a preamplifier connected to the detector 7. Thereafter, the electrical analog signal is converted into a digital signal by means of an A/D converter 11.

Next, the one-chip microcomputer 2 calculates and computes the measured glucose concentration by comparing the signal converted into a digital value by the A/D converter 11 with a calibration curve stored in the memory of the microprocessor. The resultant value is displayed on the digital display 3.

The dimensions of the above-described measurement apparatus comprising elements 1-13 illustrated in FIG. 1 may be: width×length×height under 170 mm×80 mm×25 mm, and is suitable for under 150 mm×75 mm×22 mm, among others, and more particularly, is suitable for under 130 mm×70 mm×20 mm.

A photo diode is suitable as the detector 7 and may be a germanium detector, and more particularly, may be a germanium detector connected to a preamplifier. The optical unit 6 is composed of components which shape the laser beam so that it has a diameter under 0.5~5 mm (under 2 mm among others) in order to condense and diffuse the light in parallel.

Furthermore, the present invention is not limited to an integrating sphere 9 having a globular or like shape, but it may have an oval or a half-oval cross-section or different shape.

In one embodiment of the present invention, the head can be separated from the above measurement apparatus. In this case, the light emitted from the laser diode assembly 5 can be transmitted to the head through the optic fiber, and the distance between the head and the measurement apparatus is 100~1,000 mm and is suitable for 500 mm among others, and more particularly, may be 300 mm. Of course, in another embodiment of the present invention, the head cannot be separated from the measurement apparatus.

The head assembly of the laser diode 5 is connected with the temperature controller 13 (e.g. peltier element) and with an optical unit 6 (e.g. lens system). The temperature controller 13 keeps the laser diode 5 within a stable temperature range while the optical unit 6 collimates the radiation emitted by the laser diode 5. This system consisting of the laser diode 5, temperature controller 13, and optical unit 6 is connected with the integration unit 9 so that radiation can pass through the integration unit 9 to reach human skin which is pressed against a window in the integration unit 9 The detector 7 is positioned in an opening in the integration unit 9 and detects the radiation which is absorbed, dispersed, reflected or more particularly diffusively reflected from the blood.

Usually the head assembly is integrated into the entire (small-sized) apparatus and cannot be separated from the device. For special purposes, the apparatus is modified so that the head assembly is removeable from the body of the apparatus. An optical fiber between the head assembly and body of the apparatus is used for the transport of processed data, but not for the transport of radiation required for measurement.

The present invention is not limited to a one-chip microcomputer 2 separated from the D/A converter 10 and the A/D converter 11, but can also be a one-chip microcomputer 2 which includes the D/A converter 10 and the A/D converter 11.

Moreover, in the present invention, it can be used with auxiliary circuit 12 which is composed of RAM $12_1$ and EPROM $12_2$ in order to aid the operation of one-chip microcomputer 2.

The present invention is not limited to the measurement of blood glucose concentration and, for example, can be applied to a measurement of a cholesterol concentration or an alcohol concentration.

The present invention, as above described, provides an economic method and apparatus for measuring blood glucose concentration in a non-invasive technique, which can easily measure the blood glucose concentration by putting the port of the apparatus adjacent to a part of the human body, such as the wrist, near a visible blood vessel. The present invention measures blood glucose concentration without the inconvenience and possible damage associated with drawing blood.

We claim:

1. A method for measuring blood glucose concentration comprising the steps of:
   supplying a power source from a battery to a processing means, a digital display, a laser diode power supply, a detector and an optical unit by means of a power switch;
   controlling said processing means so that said laser diode power supply gradually applies current to said laser diode at a stable voltage and temperature by means of a start/reset switch;
   controlling said processing means so that a D/A converter coupled between said processing means and said laser diode power supply converts a digital control signal provided by said processing means into an analog control signal;
   said analog control signal causing said laser diode power supply to supply current to said laser diode causing said laser diode to emit light of a wavelength appropriate for measuring a blood glucose concentration;

optically controlling, separating and combining said light emitted from said laser diode;

irradiating through an integrating sphere said optically controlled light to a blood vessel to measure said blood glucose concentration;

collecting by means of said integrating sphere said light absorbed, dispersed and diffusely reflected by blood after said light reaches said blood;

supplying said light collected by said integrating sphere to said detector which converts said light into an electrical analog signal which is supplied to a preamplifier which amplifies said electrical analog signal which is converted to a digital signal by an A/D converter;

transmitting said digital signal to said processing means;

calculating and computing said blood glucose concentration by comparing a calibration curve stored in a memory region of said processing means with said digital signal converted by said A/D converter;

displaying a calculated blood glucose concentration on said digital display.

2. The method for measuring blood glucose concentration according to claim 1, wherein said measurement method is based on an interaction between said light and a vibrational motion of blood glucose molecules in near-infrared radiation diffuse-reflection laser spectroscopy due to vibration, rotation and translation motion, utilizing overtone vibrations and a combination of other types of vibrations.

3. The method for measuring blood glucose concentration according to claim 1, wherein in the step of calculating and computing said blood glucose concentration by comparing said calibration curve stored in a memory of said processing means with said digital signal converted by said A/D converter, said method for measuring blood glucose concentration utilizes a mathematical method including a multiple linear regression analysis and a multivariate analysis.

4. An apparatus for measuring blood glucose concentration comprising:

processing means for controlling the flow of current supplied from a laser diode power supply to a laser diode assembly so that current is applied gradually and at stable voltage and temperature levels to said laser diode assembly, said processing means for calculating and computing a blood glucose concentration by comparing an electrical analog signal with a calibration curve stored in a memory of said processing means;

a D/A converter for controlling the laser diode power supply by converting a digital control signal to an analog control signal, wherein said laser diode power supply applies a power source to said laser diode assembly which comprises a light source for a blood glucose measurement, and said laser diode assembly consists of a plurality of laser diodes for emitting light of different wavelengths or emitting light of the same wavelength, in accordance with the current supplied by said laser diode power supply;

a temperature controller which controls the temperature of said plurality of laser diodes, said temperature controller being connected between said laser diode power supply and said laser diode assembly;

an optical unit which optically controls, separates or combines the light emitted from said laser diode so that the light is emitted from a port in the apparatus;

an integrating sphere which collects light dispersed and diffusely reflected from blood;

a detector which converts light from said integrating sphere into an electrical analog signal and supplies said electrical analog signal to a preamplifier which amplifies said signal; and an A/D converter which converts said electrical analog signal into a digital signal, said digital signal provided to said processing means; and a digital display connected to said processing means which displays the calculated and computed blood glucose concentration dependent upon said digital signal provided to said processing means.

5. The apparatus for measuring blood glucose concentration according to claim 4, wherein said wavelength of electromagnetic radiation emitted from said plurality of laser diodes is in the near infrared region, and said plurality laser diodes simultaneously irradiate said blood through skin.

6. The apparatus for measuring blood glucose concentration according to claim 4, wherein said wavelength of electromagnetic radiation emitted from said laser diode is between 1.3 and 1.9 microns, and said plurality of laser diodes simultaneously irradiate said blood through skin.

7. The apparatus for measuring blood glucose concentration according to claim 4, wherein said wavelength of electromagnetic radiation emitted from said plurality of laser diodes is between 1.4 and 1.8 microns, and said plurality of laser diodes simultaneously irradiate said blood through skin.

8. The apparatus for measuring blood glucose concentration according to claim 4, wherein said integrating sphere is globular in shape, said integrating sphere has a diameter of less than 2.56 cm, and said measurement apparatus has a width, length and height under 170 mm × 80 mm × 25 mm.

9. The apparatus for measuring blood glucose concentration according to claim 4, wherein said integrating sphere is globular in shape, said integrating sphere has a diameter of less than 1.28 cm, and said measurement apparatus has a width, length and height under 150 mm × 75 mm × 22 mm.

10. The apparatus for measuring blood glucose concentration according to claim 4, wherein said integrating sphere is globular in shape, said integrating sphere has a diameter of less than 0.64 cm, and said measurement apparatus has a width, length and height under 130 mm × 70 mm × 20 mm.

11. The apparatus for measuring blood glucose concentration according to claim 4, wherein said integrating sphere is oval in shape, said integrating sphere having both diameters smaller than 2.56 cm, and said measurement apparatus has a width, length and height under 170 mm × 80 mm × 25 mm.

12. The apparatus for measuring blood glucose concentration according to claim 4, wherein said integrating sphere is oval in shape, said integrating sphere having both diameters smaller than 1.28 cm, and said measurement apparatus has a width, length and height under 150 mm × 75 mm × 22 mm.

13. The apparatus for measuring blood glucose concentration according to claim 4, wherein said integrating sphere is oval in shape, said integrating sphere having both diameters smaller than 0.64 cm, and said measurement apparatus has a width, length and height under 130 mm×70 mm×20 mm.

14. The apparatus for measuring blood glucose concentration according to claim 4, wherein said integrating sphere is half oval in shape, said integrating sphere having both diameters smaller than 2.56 cm, and said measurement apparatus has a width, length and height under 170 mm×80 mm×25 mm.

15. The apparatus for measuring blood glucose concentration according to claim 4, wherein said integrating sphere is half oval in shape, said integrating sphere having both diameters smaller than 1.28 cm, and said measurement apparatus has a width, length and height under 150 mm×75 mm×22 mm.

16. The apparatus for measuring blood glucose concentration according to claim 4, wherein said integrating sphere is half oval in shape, said integrating sphere having both diameters smaller than 0.64 cm, and said measurement apparatus has a width, length and height under 130 mm×70 mm×20 mm.

17. The apparatus for measuring blood glucose concentration according to claim 4, wherein said head can be separated from said apparatus for measuring blood glucose concentration by means of an optic fiber, and the distance between the head and measurement apparatus is between 100 and 1,000 millimeters.

18. The apparatus for measuring blood glucose concentration according to claim 4, wherein said head can be separated from said apparatus for measuring blood glucose concentration by means of an optic fiber, and the distance between the head and measurement apparatus is approximately 500 millimeters.

19. The apparatus for measuring blood glucose concentration according to claim 4, wherein said head can be separated from said apparatus for measuring blood glucose concentration by means of an optic fiber, and the distance between the head and measurement apparatus is approximately 300 millimeters.

20. The apparatus for measuring blood glucose concentration according to claim 4, wherein a photo diode is utilized as said detector which detects said light collected by said integrating sphere;

said D/A converter and said A/D converter are separated from said processing means;

a battery used as said power source has potential of between 4.5 V and 9 V.

21. The apparatus for measuring blood glucose concentration according to claim 4, wherein a photo diode is utilized as said detector which detects said light collected by said integrating sphere;

said D/A converter and said A/D converter are included in said processing means;

a battery used as said power source has a potential of between 4.5 V and 9 V.

22. The apparatus of claim 20 or 21 wherein said photo diode is a germanium detector coupled to a preamplifier.

23. The apparatus for measuring blood glucose concentration according to claim 4, wherein said wavelength of electromagnetic radiation emitted from said plurality of laser diodes is in the near infrared region, and said plurality of laser diodes sequentially irradiate said blood through skin.

24. The apparatus for measuring blood glucose concentration according to claim 4, wherein said wavelength of electromagnetic radiation emitted from said laser diode is between 1.3 and 1.9 microns, and said plurality of laser diodes sequentially irradiate said blood through skin.

25. The apparatus for measuring blood glucose concentration according to claim 4, wherein said wavelength of electromagnetic radiation emitted from said plurality of laser diodes is between 1.4 and 1.8 microns, and said plurality of laser diodes sequentially irradiate said blood through skin.

* * * * *